United States Patent
Huang et al.

(10) Patent No.: US 11,261,204 B2
(45) Date of Patent: Mar. 1, 2022

(54) COMPOSITION FOR SUBSTRATE SURFACE MODIFICATION AND METHOD USING THE SAME

(71) Applicant: National Central University, Taoyuan (TW)

(72) Inventors: Chen-Han Huang, Taoyuan (TW); Wen-Hao Chen, Taoyuan (TW)

(73) Assignee: NATIONAL CENTRAL UNIVERSITY, Taoyuan (TW)

(*) Notice: Subject to any disclaimer, the term of this patent is extended or adjusted under 35 U.S.C. 154(b) by 0 days.

(21) Appl. No.: 17/011,470

(22) Filed: Sep. 3, 2020

(65) Prior Publication Data

US 2020/0399293 A1   Dec. 24, 2020

Related U.S. Application Data

(62) Division of application No. 16/531,607, filed on Aug. 5, 2019, now Pat. No. 10,975,105.

(30) Foreign Application Priority Data

Aug. 7, 2018   (TW) .................... 107127388

(51) Int. Cl.
| | | |
|---|---|---|
| *B05D 3/02* | (2006.01) | |
| *B05D 1/40* | (2006.01) | |
| *B05D 3/00* | (2006.01) | |
| *C08G 61/04* | (2006.01) | |
| *C07F 7/10* | (2006.01) | |
| *C12N 11/02* | (2006.01) | |
| *C09D 5/16* | (2006.01) | |

(52) U.S. Cl.
CPC .............. *C07F 7/10* (2013.01); *C09D 5/1662* (2013.01); *C12N 11/02* (2013.01)

(58) Field of Classification Search
CPC .......... C07F 7/10; C12N 11/02; C12N 11/08; C12N 11/14; C12N 11/06; C07K 17/14; C07K 17/06; C07K 17/08
USPC .......................... 427/384, 372.2, 331; 520/1
See application file for complete search history.

(56) References Cited

U.S. PATENT DOCUMENTS

2020/0010489 A1    1/2020  Huang et al.
2020/0048283 A1*   2/2020  Huang .................. C12N 11/08

* cited by examiner

*Primary Examiner* — Jessica Whiteley
(74) *Attorney, Agent, or Firm* — Muncy, Geissler, Olds & Lowe, P.C.

(57) ABSTRACT

The present invention provides a composition for substrate surface modification and a method using the same, and the composition for substrate surface modification is composed of a compound of the general formula structure shown in formula 1:

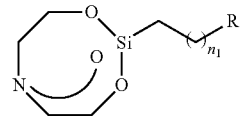

formula 1, wherein $n_1$ is an integer of 1 to 6, and R is a zwitterionic group. The composition for substrate surface modification uses water as a medium to perform modifying reaction over a substrate surface, and at the same time has biological modification characteristics, and abilities of immobilizing biomolecules and anti-biofouling.

5 Claims, 3 Drawing Sheets

COMPOSITION FOR SUBSTRATE SURFACE MODIFICATION AND METHOD USING THE SAME

CROSS REFERENCE TO RELATED APPLICATIONS

This application is a Divisional of co-pending application Ser. No. 16/531,607, filed on Aug. 5, 2019, for which priority is claimed under 35 U.S.C. § 120; and this application claims priority of Application No. 107127388 filed in Taiwan on Aug. 7, 2018 under 35 U.S.C. § 119, the entire contents of all of which are hereby 10 incorporated by reference.

FIELD OF THE INVENTION

The present invention relates to a composition for substrate surface modification, and more particularly to a compound containing a zwitterionic functional group, and a method for modifying a substrate surface under the condition of using an aqueous solution as a medium.

BACKGROUND OF THE INVENTION

The material interface interacts with biomolecules to produce the chemical or physical interaction based on the chemical properties and physical microstructures of a material, especially when a synthetic material is placed in a biological environment. For most biomolecules, the biomolecules are usually non-selectively and naturally adsorbed on the material surface. Therefore, the study of the interaction between biomolecules and material interfaces is particularly important. Among them, the control material interface has anti-specific biomolecule adsorption characteristics (hereinafter referred to as anti-biofouling), which is an indispensable part of the development of biomedical materials.

The application of zwitterionic polymers in anti-biofouling technology has been developed for many years. So far, the application of zwitterionic polymers in substrate surface modification still mainly uses gas-phase deposition method (referred to as physical vapor deposition, chemical vapor deposition) or polymer polymerized reaction method, but the processes used in the two methods are complicated and difficult to control.

When forming the zwitterionic polymer by the polymer polymerized reaction method, the chemical structure for non-specific adsorption of the material has to be considered. The design principles include: the material must be hydrophilic; the overall chemical structure must be electrically neutral; the graft density of the polymer on the surface of the material; and the physicochemical properties of the polymer bond. However, the polymer is difficult to be coated on the surface of the substrate homogeneously due to the poor hydrophilicity of the polymer bond and the high molecular weight of the polymer, which is the problem that needs to be overcome at present.

SUMMARY OF THE INVENTION

In order to solve the above problems, a main object of the present invention is to provide a composition for substrate surface modification and a method using the same, which utilize the stability and hydratability of a silatrane with a zwitterionic group for water to perform modifying reaction over a substrate surface with water as a medium.

Another main object of the present invention is to provide a method for modifying a substrate surface by using a free radical polymerization method to prepare a silatrane with a zwitterionic group. Thus, it is able to save more time and easily controls in operation by the method. In accordance with the above objects, the present invention first provides a composition for substrate surface modification composed of a compound described in formula 1:

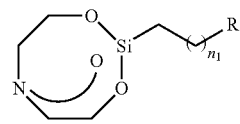

formula 1, wherein $n_1$ is an integer of 1 to 6, and R is a zwitterionic group.

In a preferred embodiment of the present invention, the zwitterionic group is selected from the group consisting of the general formulas described in formula 2-1 to formula 2-26:

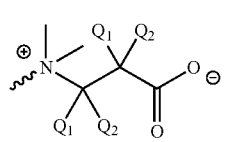

formula 2-1

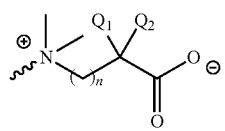

formula 2-2

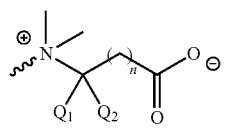

formula 2-3

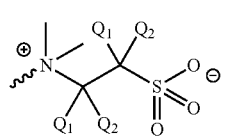

formula 2-4

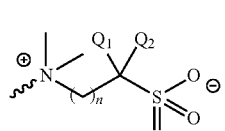

formula 2-5

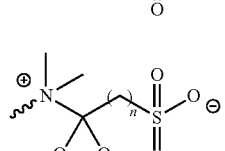

formula 2-6

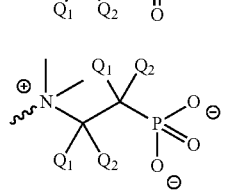

formula 2-7

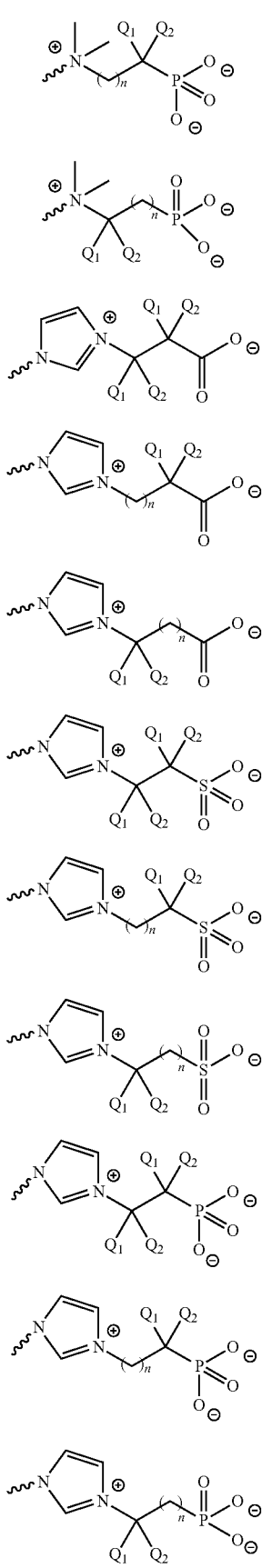

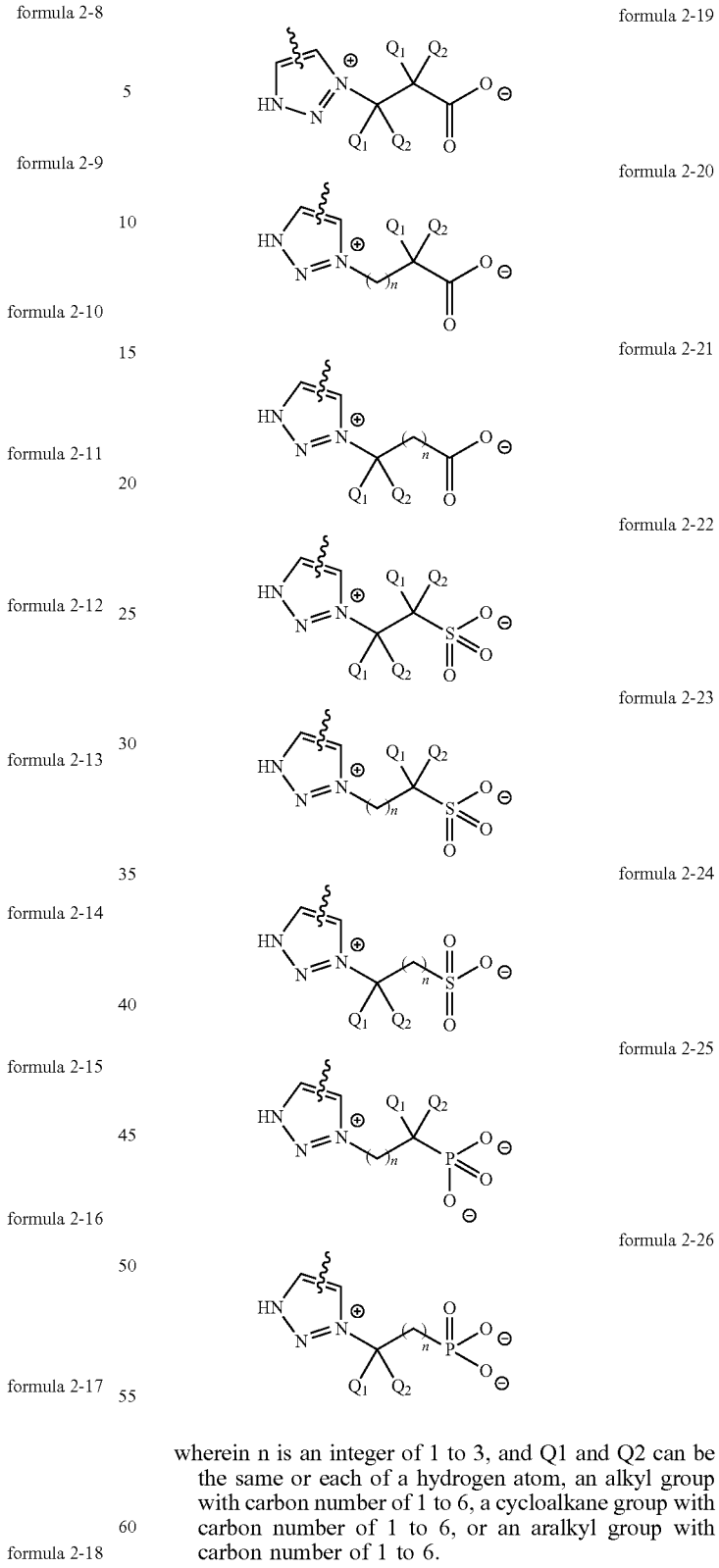

wherein n is an integer of 1 to 3, and Q1 and Q2 can be the same or each of a hydrogen atom, an alkyl group with carbon number of 1 to 6, a cycloalkane group with carbon number of 1 to 6, or an aralkyl group with carbon number of 1 to 6.

The present invention further provides a method for modifying a substrate surface, comprising: preparing a surface modification solution, providing a substrate to be surface-modified, and coating the surface modification solution on a surface of the substrate to be surface-modified for reaction to modify the surface of the substrate. The above method, wherein steps of preparing the surface modification solution comprise: providing a 2-(dimethylamino) ethyl trimethoxy silane as a reaction initiator; reacting the reaction initiator with a 3-methyloxetane-2-one to obtain an intermediate product; purifying the intermediate product to obtain a purified intermediate product; adding a triethanol amine and a toluene to react with the purified intermediate product to obtain a final reactant; adding a dimethyl sulfoxide to the final reactant to prepare a standard solution; and diluting the standard solution to form the surface modification solution.

In a preferred embodiment of the present invention, after coating the surface modification solution on the substrate surface, further comprising steps of: activating the surface of the surface-modified substrate by using 1-ethyl-3-(3-dimethylamino propyl)carbodiimide (EDC) and N-hydroxy succinimide (NHS); adding a biomolecule to be modified to the surface of the substrate for reaction; and performing a deactivating reaction by adding a buffer solution to the surface of the substrate to obtain the surface-modified substrate by the biomolecule.

According to the above, the composition for substrate surface modification and the method for modifying the substrate surface of the present invention can be used on various substrates such as metals, polymers or glass in an aqueous solution environment. By using a covalent bond force between the zwitterionic group and the biomolecules, the biomolecules are closely attached to the substrate surface. Since the ability of the biomolecule being adsorbed on the substrate surface is correlated to the graft density of the zwitterionic group, the surface of the substrate can be quickly modified and biologically modified, and has the ability of anti-biofouling.

DETAILED DESCRIPTION OF THE PREFERRED EMBODIMENTS

Figure 1:
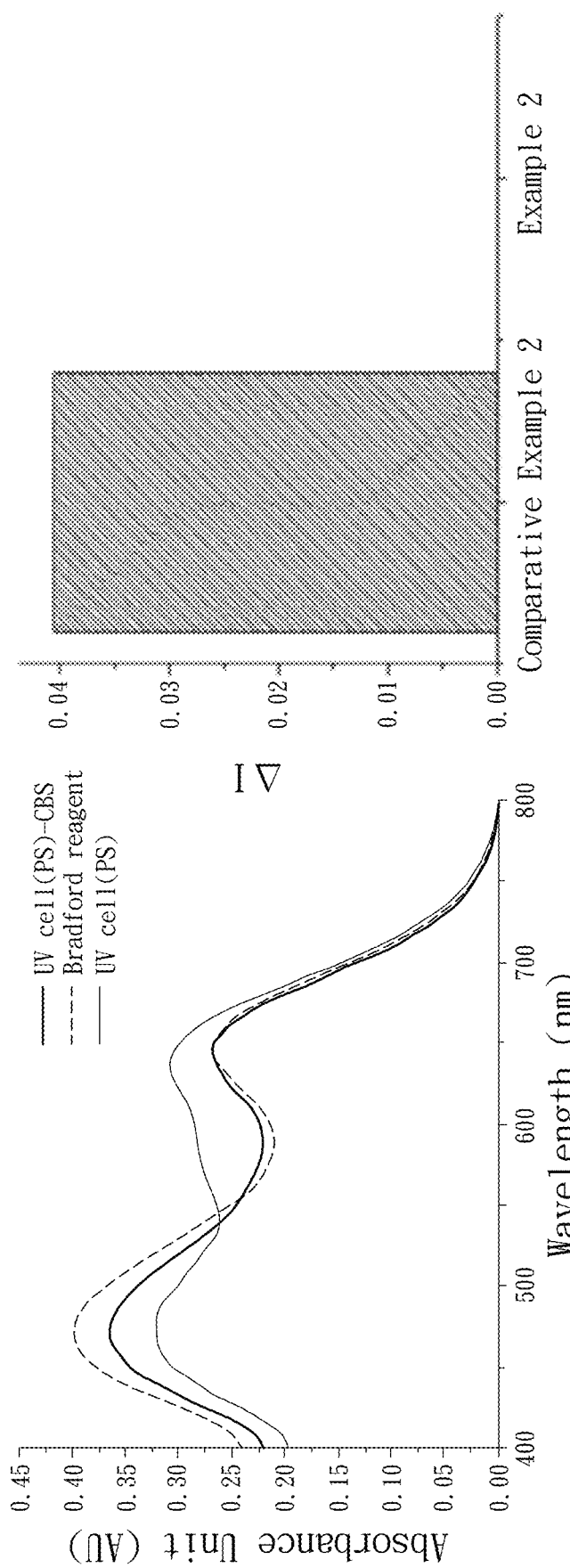
FIG. 1 is comparative graphs of the absorbance unit (AU) and the normalized absorbance intensity ($\Delta$I) for various examples.

In order to make the above and other objects, features and advantages of the present invention more comprehensible, a composition for substrate surface modification and a method using the same are described below, and related implementations and embodiments thereof are provided to illustrate the present invention and its efficacies specifically.

A main component of the composition for substrate surface modification of the present invention is a silatrane with a zwitterionic group, and the compound of the formula 1 is composed of a silatrane and a zwitterionic group.

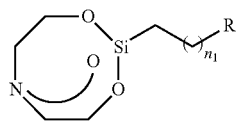

formula 1, wherein $n_1$ is an integer of 1 to 6, and R is a zwitterionic group.

In the present invention, the silatrane is a tricyclic cage symmetrical structure composed of a silicon nitride bond as a main axis, and the silatrane has water vapor tolerance and low sensitivity to water so that it is very suitable for surface bio-modification. On the contrary, silanes that have been traditionally and widely used in surface coating technology of bio-sensing will cause problems of surface aggregation and unevenness because silane functional groups are easily hydrolyzed.

The zwitterionic group comprises at least an anionic group and a cationic group. The anionic group includes a sulfo group, a carboxyl group, a phosphate group or a phosphite ester group, and the cationic group can be a primary, secondary, tertiary or quaternary amino group, a 5-membered heterocycle or a 6-membered heterocycle containing 1 oxygen atom or more than 1 nitrogen atom, for example, preferably an imidazolyl, a pyrazolyl, or a pyridyl; but is not limited thereto. The zwitterionic group can also contain other chemical groups. The anionic group and the cationic group contained in the zwitterionic group are an electronegative functional group and an electropositive functional group, respectively. When they are in an equal proportion, they are electrically neutral and can be ionically paired with the substrate surface, which is referred to a non-covalent bond, and form a covalent bond with the amino group contained in the biomolecules. Further, a strong interaction of the covalent bond and the non-covalent bond is formed on the substrate surface, so that the biomolecule is closely attached to the substrate surface. The mentioned substrate generally refers to various materials such as metals, polymers, or glass, and is not limited thereto.

In a preferred embodiment of the present invention, the zwitterionic group is selected from the group consisting of the general formulas described in formula 2-1 to formula 2-26:

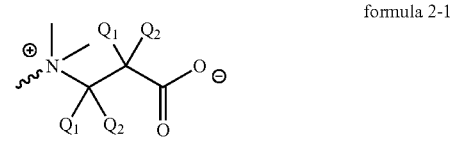

formula 2-1

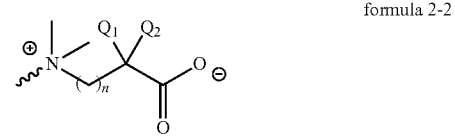

formula 2-2

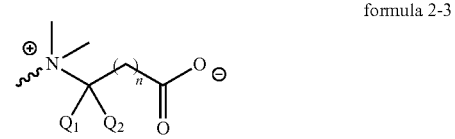

formula 2-3

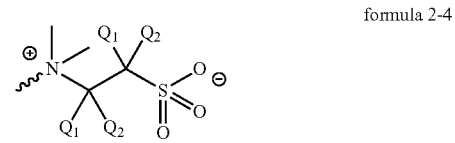

formula 2-4

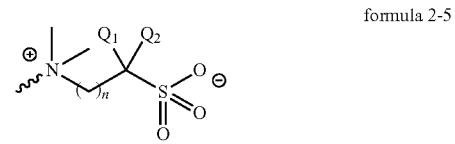

formula 2-5

-continued
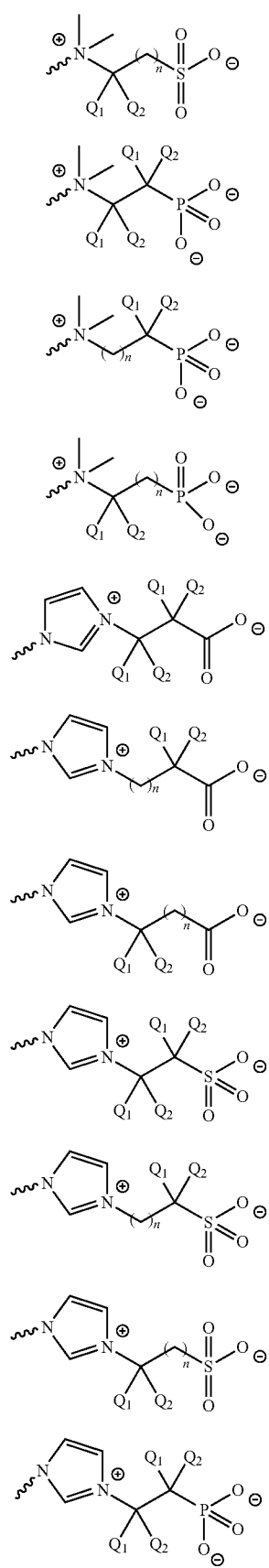
formula 2-6
formula 2-7
formula 2-8
formula 2-9
formula 2-10
formula 2-11
formula 2-12
formula 2-13
formula 2-14
formula 2-15
formula 2-16
-continued
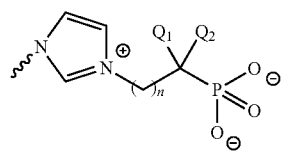
formula 2-17
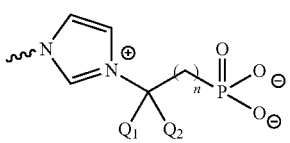
formula 2-18
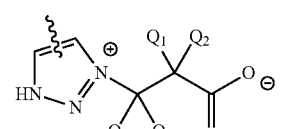
formula 2-19
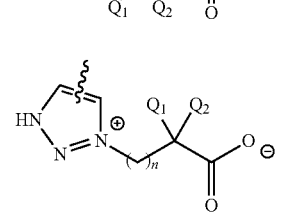
formula 2-20
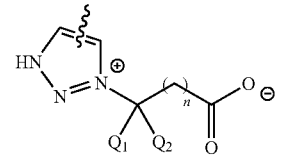
formula 2-21
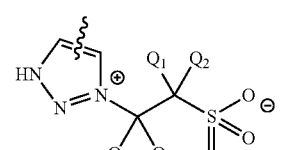
formula 2-22
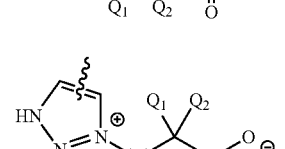
formula 2-23
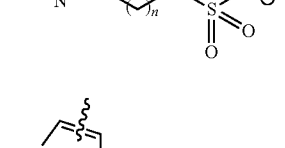
formula 2-24
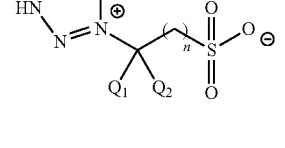
formula 2-25

-continued

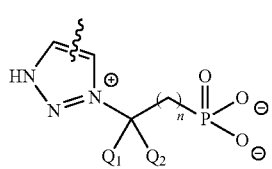

formula 2-26 wherein n is an integer of 1 to 3, and Q1 and Q2 can be the same or each of a hydrogen atom, an alkyl group with carbon number of 1 to 6, a cycloalkane group with carbon number of 1 to 6, or an aralkyl group with carbon number of 1 to 6.

According to the above composition for substrate surface modification, the present invention simultaneously provides a method of using a composition for substrate surface modification, and preferably using the composition for substrate surface modification of the present invention in an environment of water. An environment of dichloromethane or ethanol is also able to use the composition for substrate surface modification of the present invention. The main reason is that the zwitterionic group of the silatrane contained in the composition for substrate surface modification of the present invention is a hydrophilic end, and the zwitterionic group will produce a hydrogen to bond with the water or the aqueous solution of a polar solvent such as dichloromethane or ethanol; the composition for substrate surface modification is preferably grafted onto the substrate surface by water in order to adhere to the substrate surface, and various substrates such as metals, polymers or glass can be applied. Thus, this method can reduce the consumption of organic solvents and avoid damage to the surface of the substrate.

According to the above composition for substrate surface modification, the present invention simultaneously provides a method for modifying a substrate surface, which sequentially comprises steps of (S1) preparing a surface modification solution, and (S2) performing surface modification on the substrate. The foregoing steps are described in detail below.

(S1) Preparing a Surface Modification Solution

The surface modification solution of the present invention contains the silatrane with the zwitterionic group, which is a polymer formed by ring-opening polymerization. Procedure steps for preparing the surface modification solution are represented as the following reaction formula 1 to reaction formula 5, comprising step a as shown in the reaction formula 1: providing a (dimethylamino)ethyl trimethoxysilane as a reaction initiator as shown in formula 3, and reacting the reaction initiator with a 4-methyloxetan-2-one as shown in formula 4 to obtain an intermediate product. After a tertiary amino group of the 2-(dimethylamino) ethyl trimethoxy silane nucleophilically attacks the monomer of 4-methyloxetan-2-one to perform ring-opening, the pure water is added as a terminator to terminate the reaction to obtain the intermediate product as shown in formula 5; step b as shown in the reaction formula 2: purifying the intermediate product by extraction to obtain a purified intermediate product as shown in formula 5; step c as shown in the reaction formula 3: adding a triethanol amine and a toluene as shown in formula 6 to react with the purified intermediate product to obtain a final reactant as shown in formula 7; step d as shown in the reaction formula 4: adding a dimethyl sulfoxide to the final reactant to prepare a standard solution, wherein the dimethyl sulfoxide is a polar solvent and is miscible with water to stably store the final reactant; and finally, step e as shown in the reaction formula 5: diluting the standard solution with dichloromethane, ethanol or pure water to form the surface modification solution.

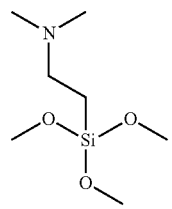

formula 3

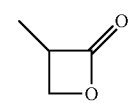

formula 4

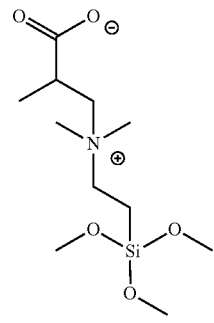

formula 5

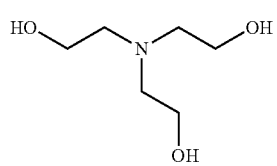

formula 6

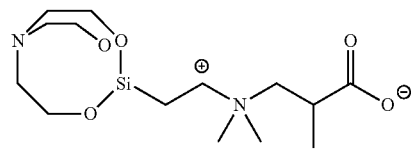

formula 7

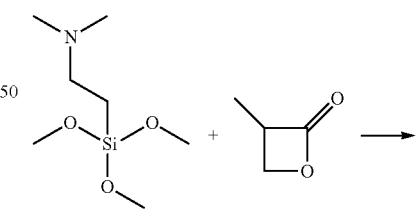

reaction formula 1

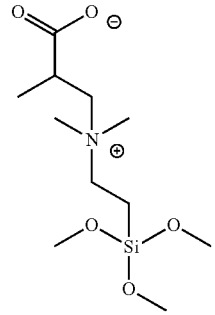

-continued

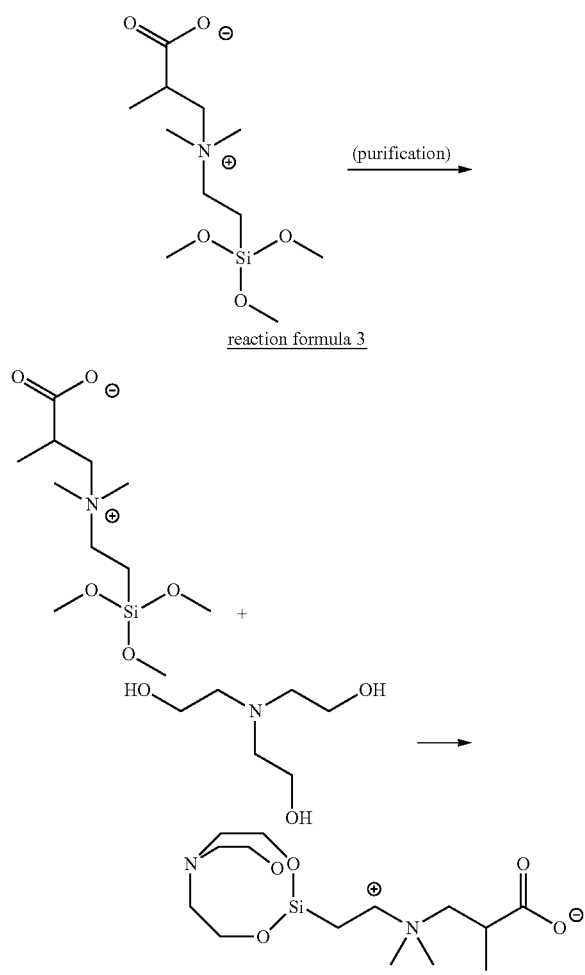

reaction formula 2

(purification)

reaction formula 3

(S2) Performing Surface Modification on the Substrate

Reacting the substrate to be surface-modified (for example, various substrates such as metals, polymers, or glass, but not limited thereto) with the surface modification solution, by immersing the substrate in the surface modification solution to react, or coating the surface modification solution on the substrate surface to react. Since the surface modification solution has strong hydratability and is able to bond with the substrate surface to produce hydroxyl interaction, the hydroxyl provides a receptor for intermolecular hydrogen bonding, and the substrate is modified to have a hydrophilic surface to resist adsorption of biomolecules. Thus, the surface-modified substrate has the ability of anti-biofouling.

In one embodiment, the present invention further provides a method for modifying a substrate surface with abilities of both bio-modification and anti-biofouling. The method sequentially comprises steps of (S1) preparing a surface modification solution; (S2) performing surface modification on the substrate; (S3) activating the surface of the surface-modified substrate; (S4) adding biomolecules to the substrate surface for reaction; and (S5) performing a deactivating reaction. Step (S1) and step (S2) are performed as described above, and will not be described again. The following describes the consequent steps.

(S3) Activating the Surface of the Surface-Modified Substrate

Activating the surface-modified substrate by using 1-ethyl-3-(3-dimethylaminopropyl)carbodiimide (EDC) and N-hydroxy succinimide (NHS), then rinsing the substrate surface with water to remove excess EDC/NHS from the environment.

(S4) Adding Biomolecules to the Substrate Surface for Reaction

Adding biomolecules to the activated substrate. Since the activated substrate has a hydrophobic surface after activation, an irreversible biomolecule adsorption layer film is formed when the activated substrate contacts with biomolecules, such as proteins, antibodies, cells, bacteria, etc. As the hydrophobic interaction between the hydrophobic end of the biomolecule structure and the substrate surface is increased, the biomolecule will be more strongly adsorbed on the substrate surface. Then, washing away the excess biomolecules with water.

(S5) Performing a Deactivating Reaction

Performing a deactivating reaction on the substrate surface adsorbed with the biomolecules with a buffer solution to obtain a substrate with a surface modified by the biomolecules. For example, the buffer solution is selected from a phosphate buffer solution, a sodium bicarbonate buffer solution, a carbonate buffer solution, preferably a phosphate buffer solution. When performing the deactivating reaction, the hydroxyl group forms a hydrogen bond with the water molecule to generate a stable hydration layer, so that biomolecule layer on the biomolecule-modified substrate retains sufficient hydration layer to prevent other types of biomolecules from getting close and being adsorbed. Therefore, the method for modifying the substrate surface of the present invention has abilities of both bio-modification and anti-biofouling.

The details of the various examples of the present invention are provided below to more clearly illustrate the present invention, but the present invention is not limited to the following examples.

Preparation Example of the Surface Modification Solution:

2-(dimethylamino) ethyl trimethoxy silane and 4-methyl-oxetan-2-one are placed in a beaker containing acetonitrile to react for 12 hours to obtain an intermediate product, and the intermediate product is purified by extraction at room temperature. Adding triethanol amine and reacting in a toluene environment for 6 hours to obtain a final reactant. Then, dimethyl sulfoxide is added to prepare a standard solution with a concentration of 1M to be stored, and the standard solution is diluted 1,000 times in water to prepare the surface modification solution with a final concentration of 1 mM.

Preparation Example of the Surface-Modified Substrate:

The surface modification solution is dip-coated on a plastic colorimetric tray to react for 30 minutes, and then the plastic colorimetric tray is rinsed with deionized water and alcohol, and dried by cold air to obtain the surface-modified substrate.

Anti-Biofouling Test:

Example 1: A bovine serum albumin solution with a high concentration (1 mg/ml) is prepared and added to the surface-modified substrate for 2 minutes. Then, the surface-modified substrate is washed with deionized water. The absorbance density (OD) at a wavelength of 590 nm is measured with a spectrometer after adding a coomassie blue reagent.

Please refer to FIG. 1. The left graph of FIG. 1 is an absorbance spectra among Example 1 according to one embodiment of the present invention, Reference Example 1, and Comparative Example 1 which are measured by a spectrometer. In the left graph of FIG. 1, the thick solid line represents the absorbance unit (AU) of Example 1, the dash line represents the absorbance unit of Reference Example 1 and the thin solid line represents the absorbance unit of Comparative Example 1 (Control experiment). Further, the right graph of FIG. 1 is a normalized absorbance intensity (ΔI) of Example 1 according to one embodiment of the present invention and Comparative Example 1.

In the left graph of FIG. 1, Comparative Example 1 (thin solid line) is a substrate without surface modification which shows the absorption of the bovine serum albumin Example 1 (thick solid line) is a substrate with surface modification according to one embodiment of the present invention, which shows no absorption of the bovine serum albumin. The absorbance curve of the Bradford reagent in Reference Example 1 (dash line) is used as a comparison baseline to demonstrate the smudge resistance to the bovine serum albumin.

In the right graph of FIG. 1, the normalized absorbance intensity at a wavelength of 590 nm of the surface-modified substrate is 0 in Example 1, indicating no bovine serum albumin is adsorbed; and the normalized absorbance intensity of Comparative Example 1 with unmodified substrate is 0.04, indicating the bovine serum albumin is adsorbed. Therefore, the plastic colorimetric tray comprising the surface-modified substrates is provided with the effect of anti-fouling against the bovine serum albumin Identification Test of Bio-Specificity:

Example 2: The Surface Modification Solution with Five different concentrations are dip-coated on five 96-well plastic plates to react for 30 minutes, then the plastic plates are rinsed with deionized water and alcohol, and dried by cold air to obtain surface-modified plastic plates. The five surface-modified plastic plates are activated and reacted with EDC/NHS for 7 minutes, then the excess EDC/NHS is washed away with deionized water. The poly Q amyloid (Heterogeneous Huntingtin protein) are respectively added into the five surface-modified plastic plates to react for 15 minutes. The excess protein is washed away with deionized water, and deactivating reaction is carried out to react for 2 minutes by adding a phosphate buffer solution with a pH of 9. Then, gold nanoparticles with specificity for the poly Q amyloid are synthesized and added onto the five plastic plates to react for 15 minutes. The absorbance of each of the plastic plates in Example 2 at a wavelength of 520 nm is measured with a spectrometer.

Comparative Example 2: The five surface-modified plastic plates are obtained in the similar manner as in Example 2. The only difference relies on that Comparative Example 2 replaces poly Q amyloid with amyloid-β ($A\beta_{1-40}$). The absorbance of each of the plastic plates in the Comparative Example 2 at a wavelength of 520 nm is measured with a spectrometer.

Figure 2:
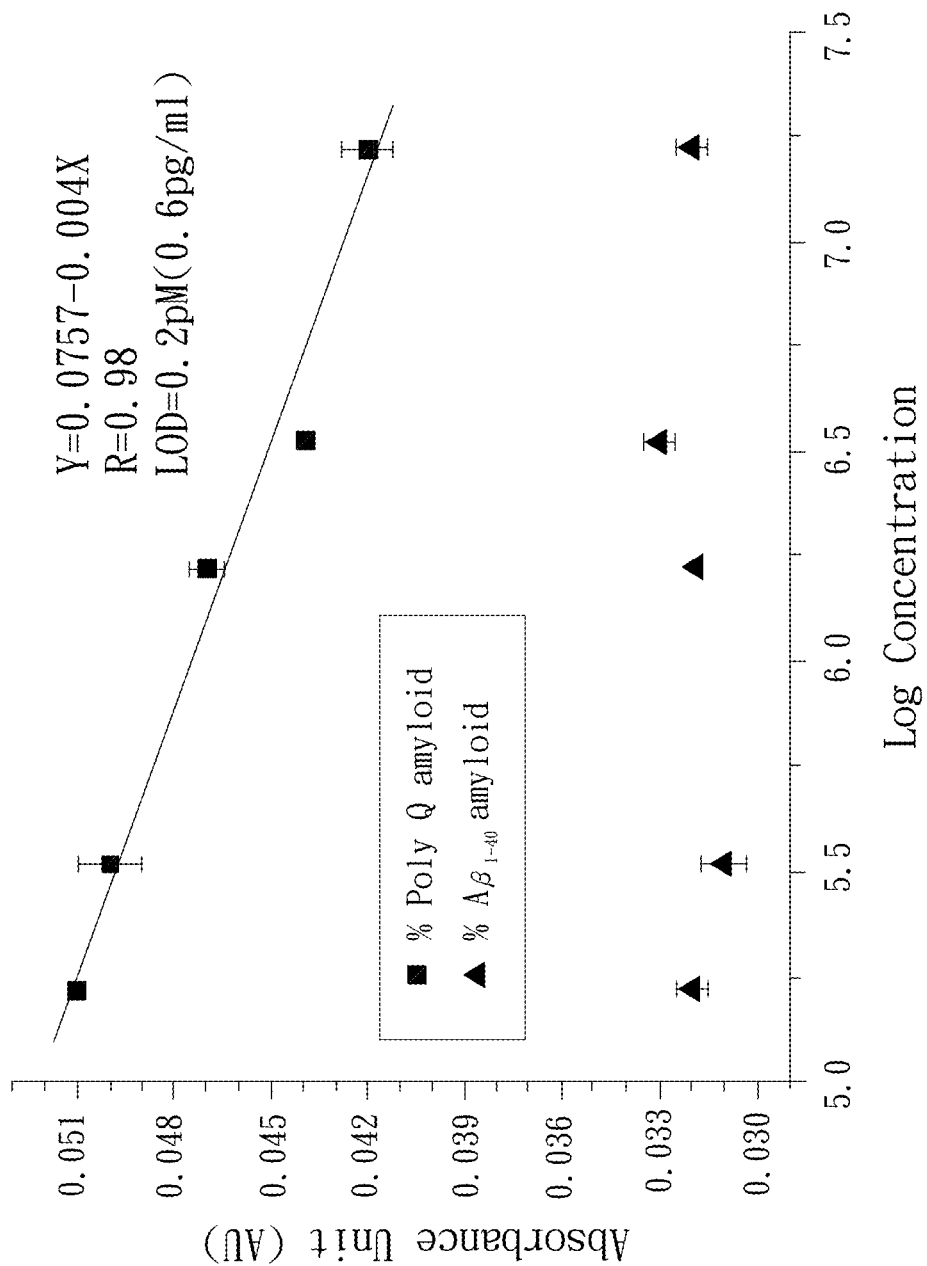
FIG. 2 is a graph of linear regression of the analysis of the absorbance of Example 2 and Comparative Example 2 measured by a spectrometer according to an embodiment of the present invention.

Accordingly, the absorbance data of the surface-modified plastic plates added with poly Q amyloid and $A\beta_{1-40}$ are respectively obtained from the Example 2 and Comparative Example 2, and the absorbance data of the surface-modified plastic plates are applied to run a linear regression analysis respectively. FIG. 2 is a graph of linear regression of the absorbance between Example 2 and Comparative Example 2 measured by a spectrometer. It can be known that the absorbance unit of the surface-modified plastic plates added with the poly Q amyloid varies depending on the concentrations of the surface-modified plastic plates. However, the absorbance unit of the surface-modified plastic plates added with the $A\beta_{1-40}$ are not changed with the concentrations of the surface-modified plastic plates. Thus, the surface-modified plastic plates in Example 2 have an identification ability of bio-specificity to the poly Q amyloid. That is, the concentration of adsorbed poly-Q amyloid is correlated to the concentration of the surface modification on the plastic plate. The absorbance shows a good linear relationship with the concentrations, which means that the detection limit is clearly known, and the surface-modified plastic plates comprising in Example 2 is provided with high detection sensitivity.

Test of Specificity of Immunoreaction:

Example 3: Five surface-modified 96-well plastic plates are obtained in the same manner as in Example 2. The surface-modified plastic plates are activated and reacted by EDC/NHS for 7 minutes, then the excess EDC/NHS is washed away with deionized water, and 0.01 ppm of an anti-mouse antibody is added to react for 15 minutes. The excess anti-mouse antibody is washed away with deionized water, and deactivating reaction is carried out for 2 minutes by adding a phosphate buffer solution with a pH of 9 to complete modification of the surfaces of the plastic plates by the anti-mouse antibody. Then, the five plastic plates modified with the anti-mouse antibody (used as an antibody) are added with mouse antibody of five different concentrations to react for 15 minutes, the logarithmic concentrations of the mouse antibody (used as an antigen) are respectively 6.3, 6.0, 5.7, 5.4, 5.1. Further, a coomassie blue reagent is added to measure the absorbance each of the plastic plates at a wavelength of 595 nm with a spectrometer.

Figure 3:
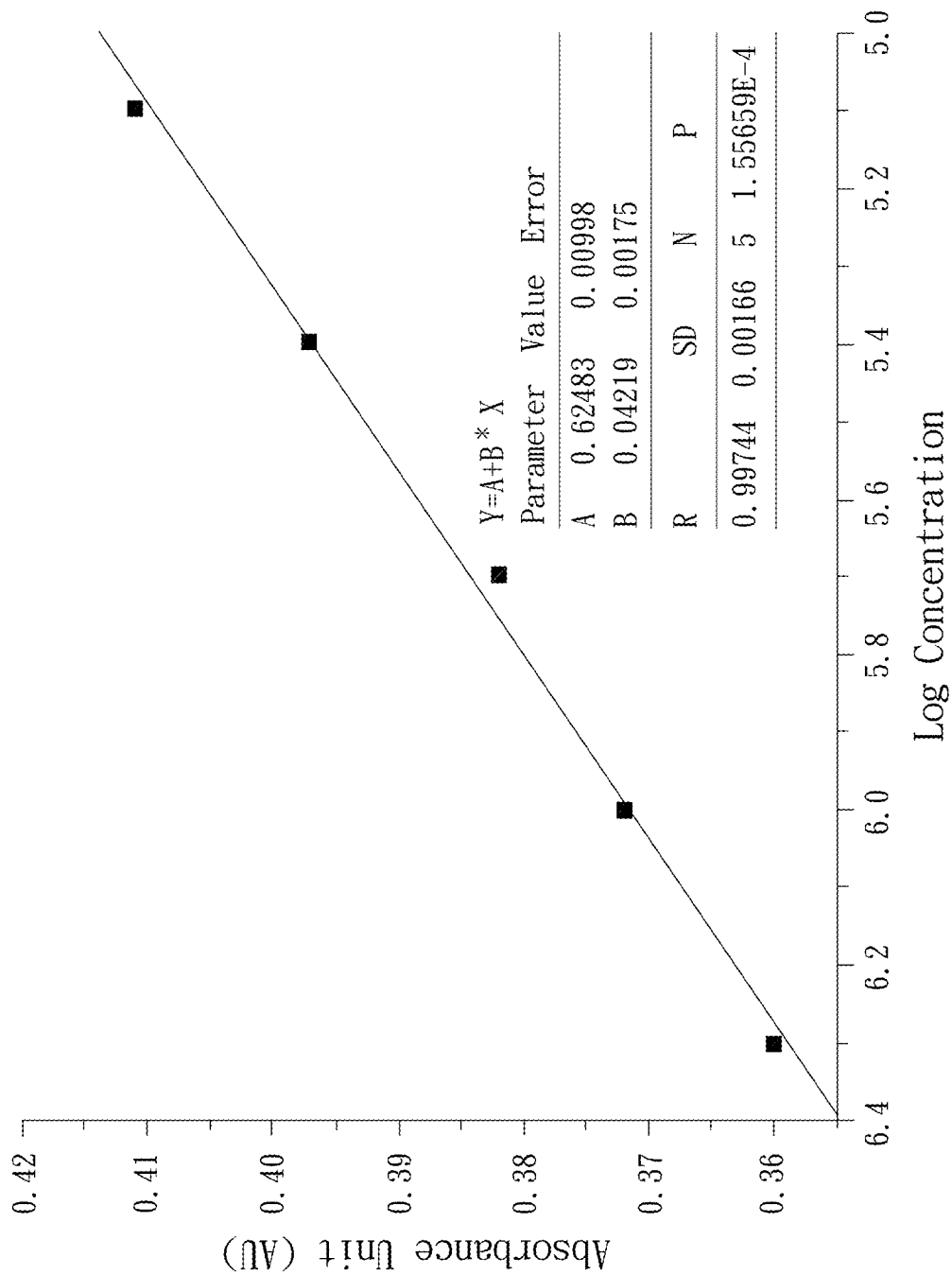
FIG. 3 is a graph of linear regression of the analysis of the absorbance of Example 3 measured by a spectrometer according to an embodiment of the present invention.

Five sets of absorbance data corresponding to different antigen concentrations are obtained, and linear regression is performed as shown in FIG. 3. FIG. 3 is a graph of linear regression of the analysis of the absorbance of Example 3 measured by a spectrometer, and the antigen concentrations show a good linear relationship with the absorbance Thus, the plastic plates comprising the surface-modified substrates in Example 3 is able to sense the specific immunoreaction of the antibodies to the antigens, which can be applied to bio sensing and biomedical materials.

In summary, the composition for substrate surface modification of the present invention allows the substrate surface being modified by water, so that the substrate will not be contaminated by organic solvents. At the same time, the substrate surface has biological modification characteristics, the ability to immobilize biomolecules, and anti-biofouling characteristics, such as anti-protein adsorption control, anti-blood coagulation control, anti-tissue adhesion control, anti-bacterial control, etc.; Besides, after activation by EDC/NHS, the substrate surface can be biologically modified, so that the substrate surface has a high compatibility with biomolecules, a high identification ability of bio-specificity, and can sense immunoreaction, which is considerably suitable for using in biomedical materials for, such as biomimetic engineering, bio-inspiration, and biological sensing.

What is claimed is:

1. A method for modifying a substrate surface, comprising:
    preparing a surface modification solution, comprising:
        providing a 2-(dimethylamino) ethyl trimethoxy silane as a reaction initiator;
        reacting the reaction initiator with a 4-methyloxetan-2-one to obtain an intermediate product;
        purifying the intermediate product to obtain a purified intermediate product;

adding a triethanol amine and a toluene to react with the purified intermediate product to obtain a final reactant;

adding a dimethyl sulfoxide to the final reactant to prepare a standard solution; and diluting the standard solution to form the surface modification solution;

providing a substrate to be surface-modified; and coating the surface modification solution on a surface of the substrate to be surface-modified for reaction to modify the surface of the substrate.

2. The method for modifying the substrate surface as claimed in claim 1, wherein the reaction initiator is reacted with the 4-methyloxetan-2-one in an acetonitrile solution.

3. The method for modifying the substrate surface as claimed in claim 1, wherein the step of diluting the standard solution comprises using dichloromethane, ethanol or pure water to dilute.

4. The method for modifying the substrate surface as claimed in claim 1, wherein the substrate is a metal, a polymer or a glass.

5. The method for modifying the substrate surface as claimed in claim 1, wherein after coating the surface modification solution on the surface of the substrate, the method further comprises steps of:

activating the surface of the surface-modified substrate using 1-ethyl-3-(3-dimethylaminopropyl)carbodiimide (EDC) and N-hydroxy succinimide (NHS);

adding a modifying biomolecule to the surface of the substrate for reaction; and performing a deactivating reaction by adding a buffer solution to the surface of the substrate to obtain the surface-modified substrate by the biomolecule.

* * * * *